United States Patent [19]

Schudok

[11] Patent Number: 5,962,471

[45] Date of Patent: Oct. 5, 1999

[54] SUBSTITUTED 6- AND 7-AMINOTETRAHYDRO-ISOQUINOLINECARBOXYLIC ACIDS

[75] Inventor: Manfred Schudok, Eppstein/Ts, Germany

[73] Assignee: Hoechst Aktiengesellschaft, Frankfurt, Germany

[21] Appl. No.: 09/075,186

[22] Filed: May 11, 1998

[30] Foreign Application Priority Data

May 13, 1997 [DE] Germany ............... 197 19 817

[51] Int. Cl.⁶ .............. A61K 31/47; A61K 31/475; C07D 217/22; C07D 217/00
[52] U.S. Cl. .............. 514/309; 546/141; 546/143; 546/146; 546/147
[58] Field of Search .............. 514/309; 546/141, 546/143, 146, 147

[56] References Cited

U.S. PATENT DOCUMENTS

| | | | |
|---|---|---|---|
| 4,613,606 | 9/1986 | Clark et al. | 514/307 |
| 4,681,889 | 7/1987 | Clark et al. | 514/307 |
| 5,393,760 | 2/1995 | Ackermann et al. | 514/323 |
| 5,455,258 | 10/1995 | MacPherson | 514/357 |
| 5,506,242 | 4/1996 | MacPherson | 514/336 |
| 5,506,258 | 4/1996 | Christophe et al. | 514/423 |
| 5,532,232 | 7/1996 | Ackermann et al. | 514/183 |
| 5,552,419 | 9/1996 | MacPherson | 514/357 |
| 5,583,133 | 12/1996 | Ackermann et al. | 514/183 |
| 5,595,999 | 1/1997 | Ackermann et al. | 514/309 |
| 5,674,890 | 10/1997 | Christophe et al. | 514/438 |
| 5,714,497 | 2/1998 | Christophe et al. | 514/307 |

FOREIGN PATENT DOCUMENTS

| | | |
|---|---|---|
| 0 305 947 | 3/1989 | European Pat. Off. . |
| 0 468 231 | 1/1992 | European Pat. Off. . |
| 0 606 046 | 7/1994 | European Pat. Off. . |
| 0 614 911 | 9/1994 | European Pat. Off. . |
| 197312 | 12/1986 | Hungary . |
| WO 95/29892 | 11/1995 | WIPO . |
| WO 95/35276 | 12/1995 | WIPO . |
| WO 96/00214 | 1/1996 | WIPO . |
| WO 96/27583 | 9/1996 | WIPO . |
| WO 96/33172 | 10/1996 | WIPO . |
| WO 97/18194 | 5/1997 | WIPO . |
| WO 97/49674 | 12/1997 | WIPO . |

OTHER PUBLICATIONS chemical Abstracts 113:6182, abstract of JP 02009863, Okada, 1990.
Chemical Abstracts 128:102014, abstract of WO 9800403, Dominianni, 1998.
chemical Abstracts 127:65701, abstract of WO 9718194, Thorwart, 1997.
Fosang et al., "Aggrecan is Degraded by Matrix Metalloproteinases in Human Arthritis," J. Clin. Invest., 98(10):2292–2299 (1996).
CA 112:76983, Tripathi, 1989.

*Primary Examiner*—D M Mach
*Attorney, Agent, or Firm*—Finnegan, Henderson, Farabow, Garrett & Dunner, L.L.P.

[57] ABSTRACT

Compounds of the formula I

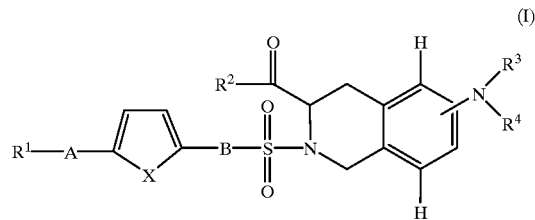

are suitable for the preparation of pharmaceuticals for the prophylaxis and therapy of disorders involving increased activity of matrix-degrading metalloproteinases.

13 Claims, No Drawings

SUBSTITUTED 6- AND 7-AMINOTETRAHYDRO-ISOQUINOLINECARBOXYLIC ACIDS

THE FIELD OF THE INVENTION

The invention relates to novel substituted 6- and 7-aminotetrahydroisoquinolinecarboxylic acids, processes for their preparation and use thereof as pharmaceuticals.

DESCRIPTION OF THE PRIOR ART

The Applications EP 0 606 046, WO 95/35276 and WO 96/27583 describe arylsulfonylaminohydroxamic acids and their action as matrix metalloproteinase inhibitors. Specific arylsulfonylaminocarboxylic acids are used as intermediates for the preparation of thrombin inhibitors (EP 0 468 231) and aldose reductase inhibitors (EP 0 305 947). The Application EP 0 757 037 also describes the action of sulfonylamino acid derivatives as metalloproteinase inhibitors. The disclosures of all these documents are incorporated herein by reference.

SUMMARY OF THE INVENTION

The invention relates to substituted 6- and 7-aminotetrahydroisoquinolinecarboxylic acids of the formula I:

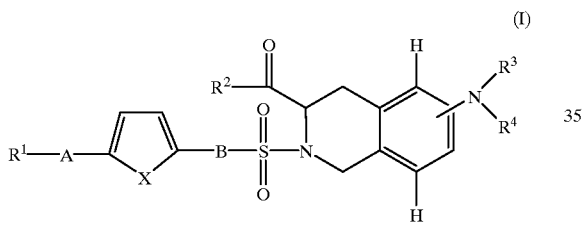

(I)

Compounds of the formula I are suitable for the preparation of pharmaceuticals or the prophylaxis and therapy of disorders involving increased activity of matrix-degrading metalloproteinases. In particular, the compounds are useful for preventing or treating degenerative joint disorders, disorders of the connective tissue, ulcerations, atherosclerosis, stenosis, inflammation, carcinamoatosis, formation of tumor metastases, cachexi, anorexia, and septic shock.

DESCRIPTION OF THE PREFERRED EMBODIMENTS

In the effort to find efficacious compounds for the treatment of connective tissue disorders, it has now been found that the carboxylic acids according to the invention are strong inhibitors of the matrix metalloproteinases. Particular value is placed here on the inhibition of stromelysin (matrix metalloproteinase 3) and of the neutrophil collagenase (MMP-8), since both enzymes are substantially involved, in particular, in the degradation of the proteoglycans, as important constituents of the cartilagenous tissue (A. J. Fosang et al. J. Clin. Invest. 98 (1996) 2292–2299). The disclosure of this document is incorporated herein by reference.

The invention therefore relates to the compounds of the formula I

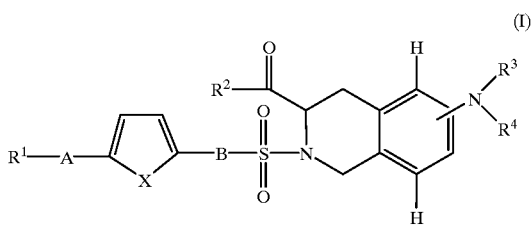

(I)

and/or a stereoisomeric form of the compounds of the formula I and/or a physiologically tolerable salt of the compounds of the formula I and/or their stereoisomeric forms, where $R^1$ is 1. phenyl;
  2. phenyl which is mono- or disubstituted by
    2.1. $(C_1-C_6)$-alkyl, which is linear, cyclic or branched,
    2.2. —OH,
    2.3. $(C_1-C_6)$-alkyl-C(O)—O—,
    2.4. $(C_1-C_6)$-alkyl-O—,
    2.5. $(C_1-C_6)$-alkyl-O—$(C_1-C_4)$-alkyl-O—,
    2.6. halogen,
    2.7. —$CF_3$,
    2.8. —CN,
    2.9. —$NO_2$,
    2.10. HO—C(O)—,
    2.11. $(C_1-C_6)$-alkyl-O—C(O)—,
    2.12. methylenedioxo,
    2.13. $R^5$—$(R^6)$N—C(O)—, in which $R^5$ and $R^6$ are identical or different and represent a hydrogen atom or $(C_1-C_6)$-alkyl-, or
    2.14. $R^5$—$(R^6)$N—, in which $R^5$ and $R^6$ are identical or different and represent a hydrogen atom or $(C_1-C_6)$-alkyl-;
  3. a heteroaromatic from the following group 3.1. to 3.15., which is unsubstituted or substituted as described under 2.1 to 2.14,
    3.1. pyrrole,
    3.2. pyrazole,
    3.3. imidazole,
    3.4. triazole
    3.5. thiophene,
    3.6. thiazole,
    3.7. oxazole,
    3.8. isoxazole,
    3.9. pyridine,
    3.10. pyrimidine,
    3.11. indole,
    3.12 benzothiophene,
    3.13. benzimidazole,
    3.14. benzoxazole, or
    3.15. benzothiazole;
  4. —OH and A is a covalent bond;
  5. —O—$R^{14}$ and A is a covalent bond, —CH=CH— or —C≡C—
    and in which $R^{14}$ is
    1) $(C_1-C_6)$-alkyl,
    2) $(C_3-C_6)$-cycloalkyl,
    3) benzyl, or
    4) phenyl;
  6. —COOH and A is a covalent bond, —CH=CH— or —C≡C—;
  7. $(C_1-C_6)$-alkyl;
  8. $(C_3-C_6)$-cycloalkyl-O-$(C_1-C_4)$-alkyl;
  9. halogen and A is a covalent bond, —CH=CH— or —C≡C—;

10. —CN and A is a covalent bond, —CH=CH— or —C≡C—;
11. —NO₂ and A is a covalent bond, —CH=CH— or —C≡C—; or
12. —CF₃;

R² is 1. HO(H)N—; or
2. R⁷—O—, in which R⁷ is
   2.1 a hydrogen atom,
   2.2 (C₁–C₆)-alkyl,
   2.3 allyl, or
   2.4 benzyl;

R³ and R⁴ are identical or different and are
1. hydrogen;
2. (C₁–C₆)-alkyl;
3. phenyl-(CH₂)ₘ, in which phenyl is unsubstituted or mono- or disubstituted as described under 2.1 to 2.14. and m is the integer zero, 1, 2, or 3;
4. R⁸—(CO)—, in which R⁸ is
   4.1 (C₁–C₈)-alkyl,
   4.2 phenyl-(CH₂)ₘ—, in which phenyl is unsubstituted or mono- or disubstituted as described under 2.1. to 2.14. and m is the integer zero, 1, 2, or 3,
   4.3 R⁷—O—C(O)—(CH₂)ₙ—, in which R⁷ is as defined above and n is the integer zero, 1, 2, 3, 4, 5, or 6,
   4.4 R⁷—N(H)—(R⁹)—C(H)—, in which R⁷ is as defined above and R⁹ is the characteristic radical of a proteinogenic α-amino acid and in which R⁹ is unsubstituted or mono- or disubstituted on an oxygen or sulfur atom by (C₁–C₄)-alkyl, benzyl or allyl or is substituted by an N-protective group,
   4.5 R⁷—C(O)—N(H)—(R⁹)—C(H)—, in which R⁷ and R⁹ are as defined under 4.4, or
   4.6 R¹⁰—O—C(O)—N(H)—(R⁹)—C(H)—, in which R⁹ is as defined under 4.4 and R¹⁰ is
      4.6.1 (C₁–C₆)-alkyl,
      4.6.2 allyl,
      4.6.3 benzyl, or
      4.6.4 (9-fluorenyl)methyl;
5. R¹⁰—O—C(O)—, in which R¹⁰ is as defined under 4.6.1 to 4.6.4;
6. R¹⁵—SO₂—, in which R¹⁵ is
   6.1 (C₁–C₆)-alkyl,
   6.2 allyl, or
   6.3 phenyl-(CH₂)ₘ—, in which phenyl is unsubstituted or mono- or disubstituted as described under 2.1 to 2.14 and m is the integer zero, 1, 2 or 3; or
7. H₂N—C(=NH)—; or R³ and R⁴ together with the nitrogen atom form a radical of the formula Xₐ or X_b,

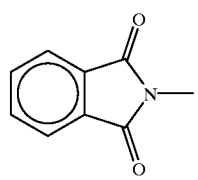
(Xₐ)

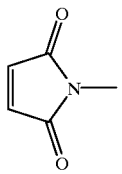
(X_b)

or

R³ and R⁴ together with the nitrogen atom form a nitro radical;

A is a) a covalent bond,
   b) —O—,
   c) —CH=CH—, or
   d) —C≡C—;

B is a) —(CH₂)ₘ—, in which m has the abovementioned meaning,
   b) —O—(CH₂)_q, in which q is the integer 1, 2, 3, 4, or 5, or
   c) —CH=CH—; and X is —CH=CH—, oxygen, or sulfur.

As used in the specification, the term "halogen" is understood as meaning fluorine, chlorine, bromine, or iodine. The term "alkyl" or "alkenyl" is understood as meaning hydrocarbon radicals whose carbon chains may be straight-chain or branched. Furthermore, the alkenyl radicals can contain several double bonds. Cyclic alkyl radicals are, for example, 3- to 6-membered monocycles, such as cyclopropyl, cyclobutyl, cyclopentyl, or cyclohexyl. The expression "R⁹ is the characteristic radical of a proteinogenic amino acid" is understood as meaning radicals R of the formula X_c,

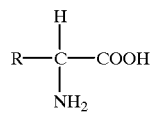
(X_c)

in which R is derived from the amino acids glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid and both enantiomeric forms as well as the racemate or any desired mixture can be employed.

The invention further relates to a process for the preparation of the compounds of the formula I and/or a stereoisomeric form of the compounds of the formula I and/or a physiologically tolerable salt of the compounds of the formula I and/or its steroisomers. The starting substances of the chemical reactions are known or can be easily prepared by methods known from the literature. The preparation process comprises the steps of:

a) converting the compound of the formula II

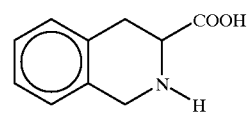
(II)

into a compound of the formula III,

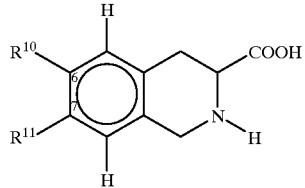

(III)

in which $R^{10}$ and $R^{11}$ are —$NO_2$ or a hydrogen atom and $R^{10}$ and $R^{11}$ are not identical, and b) reacting the compound of the formula III obtained in a) with the compound of the formula IV

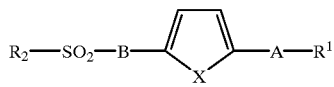

(IV)

in which B, X, A, and $R^1$ are as defined in formula I and $R_2$ is a chlorine atom, imidazolyl, or —OH, in the presence of a base or, if appropriate, a dehydrating agent to give a compound of the formula V

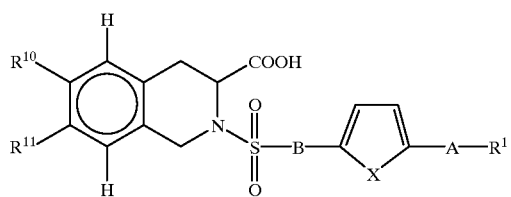

(V)

in which $R^{10}$ and $R^{11}$ are —$NO_2$ or a hydrogen atom and $R^{10}$ and $R^{11}$ are not identical, and c) subjecting the compound of the formula V obtained in b) to an isomer separation and obtaining a compound of the formula I in which $R^3$ and $R^4$ together with the nitrogen atom form an $NO_2$ radical which binds to the phenyl radical in position 6 or 7, or d) reducing the compound obtained in c) to a compound of the formula I in which $R^3$ and $R^4$ are hydrogen, or e) acylating a compound obtained in d) with carbonyl or sulfonyl chlorides, carboxylic or sulfonic imidazolides, chloroformic acid esters, active esters or anhydrides, or f) reacting a compound obtained in d) with the appropriate amino acid, carboxylic acid, aldehyde or an optionally substituted guanidine, or g) alkylating a compound obtained in d), or h) reacting a compound obtained in a) to give a compound of the formula VI,

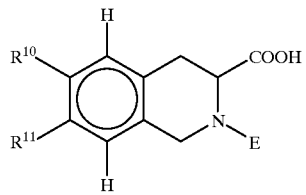

(VI)

in which E is an N-protective group and $R^{10}$ and $R^{11}$ are as defined above, and separating the compound of the formula VI into the regioisomers of the formulae VII and VIII

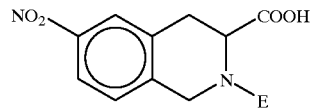

(VII)

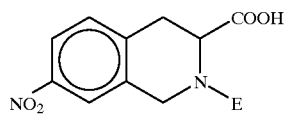

(VIII)

and reacting the nitro group as described under d) and reacting the compound obtained as under e), f), or g), i) reacting a compound obtained by the process d), e), f), g), or h) to give the corresponding carboxylic acid ester ($R^2$=O—$R^7$), or j) reacting a compound obtained by the process d), e), f), g), or h) with hydroxylamine ($R^2$=—N(H)—OH).

As discussed in connection with the preparation of the compounds of formula I, suitable N-protective groups (referred to as "E") include the N-protective groups customarily used in peptide chemistry, for example protective groups of the urethane type, such as benzyloxycarbonyl(Z), t-butyloxycarbonyl ("Boc"), 9-fluorenylmethoxycarbonyl ("Fmoc") and allyloxycarbonyl ("Aloc") or of the acid amide type, in particular formyl, acetyl or trifluoroacetyl, or of the alkyl type such as benzyl. The (trimethylsilyl) ethoxycarbonyl ("Teoc") group has proven particularly suitable therefor. Furthermore, the alkenyl radicals can also contain several double bonds. See P. Kociénski, *Protecting Groups*, Thieme Verlag 1994.

The invention also relates to pharmaceuticals which contain an effective amount of at least one compound of the formula I and/or an optionally stereoisomeric form of the compounds of the formula I, and/or of a physiologically tolerable salt of the compounds of the formula I or their stereoisomeric forms, together with a pharmaceutically suitable and physiologically tolerable excipient, additive and/or other active compounds and auxiliaries.

On account of the pharmacological properties, the compounds according to the invention are suitable for the prophylaxis and therapy of all those involving an increased activity of matrix-degrading metalloproteinases. These include degenerative joint disorders such as osteoarthroses, spondyloses, chondrolysis after joint traumas or relatively long immobilization of the joint after meniscus or patella injuries or tears of the ligaments. Furthermore, these also include disorders of the connective tissue such as collagenoses, periodontal disorders, wound healing disorders, and chronic disorders of the locomotory apparatus (such as inflammatory, immunologically or metabolically related acute and chronic arthritides, arthropathies, myalgias and disorders of the bone metabolism). The compounds of the formula I are also suitable for the treatment of ulceration, atherosclerosis, and stenoses. The compounds of the formula I are furthermore suitable for the treatment of inflammations, carcinomatous disorders, formation of tumor metastases, cachexia, anorexia, and septic shock.

The pharmaceuticals according to the invention are in general administered orally or parenterally. Rectal or transdermal administration is also possible. The invention also relates to a process for the production of a pharmaceutical, which comprises bringing at least one compound of the formula I into a suitable administration form using a pharmaceutically suitable and physiologically tolerable excipient and, if appropriate, other suitable active compounds, additives, or auxiliaries.

Suitable solid pharmaceutical preparation forms are, for example, granules, powders, coated tablets, tablets, (micro) capsules, suppositories, syrups, juices, suspensions, emulsions, drops or injectable solutions and also preparations with protracted release of active compound, in whose preparation customary auxiliaries, such as excipients, disintegrants, binders, coating agents, swelling agents, glidants or lubricants, flavorings, sweeteners, or solubilizers are used. Frequently used auxiliaries which may be included are magnesium carbonate, titanium dioxide, lactose, mannitol and other sugars, talc, lactoprotein, gelatin, starch, cellulose and its derivatives, animal and vegetable oils (such as fish liver, sunflower, groundnut or sesame oil), polyethylene glycol and solvents such as, for example, sterile water and mono- or polyhydric alcohols (e.g. glycerol).

The pharmaceutical preparations are preferably prepared and administered in dose units, each unit as active constituent containing a specific dose of the compound of the formula I according to the invention. In solid dose units such as tablets, capsules, coated tablets or suppositories, this dose can be up to approximately 1000 mg, but preferably approximately 50 to 300 mg, and in injection solutions in ampoule form up to approximately 300 mg, preferably approximately 10 to 100 mg.

For the treatment of an adult patient weighing approximately 70 kg—depending on the efficacy of the compounds according to formula I, daily doses of approximately 20 mg to 1000 mg of active compound, preferably approximately 100 mg to 500 mg, are indicated. Under certain circumstances, however, higher or lower daily doses may be appropriate. The daily dose can be administered both by single administration in the form of an individual dose unit or else of several smaller dose units and by multiple administration of subdivided doses at specific intervals.

$^1$H-NMR spectra have been recorded on a 200 MHz apparatus from Varian or a 400 MHz apparatus from Bruker, as a rule using tetramethylsilane (TMS) as an internal standard and at room temperature (RT). The solvent used was DMSO-$d_6$ in each case, if not noted otherwise. As a rule, final products are determined by mass spectroscopic methods (FAB-, ESI-MS). Temperature data in degrees Celsius, RT means room temperature (20° C.–26° C.). Abbreviations used are either explained or correspond to the customary conventions.

EXAMPLE 1

(6/7)-Nitro-1,2,3,4-tetrahydroisoquinoline-(R)-3-carboxylic acid 100 g of 1,2,3,4-tetrahydroisoquinoline-3-carboxylic acid (564 mmol) are dissolved or suspended in 500 ml of sulfuric acid (98% strength, d 1.84) at −10° C. and cooled to −30° C. 59 g (584 mmol) of potassium nitrate, dissolved in 200 ml of sulfuric acid and cooled to 0° C., are then added dropwise in the course of 1.5 hours (h). The internal temperature rises again to −10° C. in this process. After completion of the addition of nitrate, the mixture is additionally stirred for 10 min at −10° C. and for 1 h without external cooling. The mixture is poured onto ice and neutralized with concentrated aqueous ammonia solution with cooling; consumption approximately 1.8 l of the 25% strength solution. Before filtering off the amino acid, the mixture is diluted with the same volume of water. The solid obtained is again suspended in water and filtered off from residual soluble ammonium salts. It is washed with plenty of cold water and dried at 60° C. under reduced pressure.

Yield: 110.1 g (88% of theory); Melting point: from 245° C. (slow discoloration), 272–2750° C. (melts with decomposition); $^1$H-NMR: (400 MHz, DCl/D$_2$O) 3.05 (dd, 1 H, 7-isomer); 3.30 (2 dd, superimposed, 2 H, 6- and 7-isomer); 3.44 (dd, "1 H", 6-isomer); 4.25 (m, 3 H); 7.20; 7.80 (2 m, 3 H); proportion of the 6-isomer: 13%; Elemental analysis: C 53.9 (theor. 54.06), H 4.50 (theor. 4.55), N 12.6 (theor. 12.61); IR: 1640 (s), 1540 (s), 1400 (s), 1350 (s) cm−1

EXAMPLE 2 tert-Butoxycarbonyl-(6/7)-nitro-1,2,3,4-tetrahydroisoquinoline-(R)-3-carboxylic acid 13.3 g (59.9 mmol) of the compound from Example 1 are dissolved or suspended in 300 ml of dioxane/water 1:1 with 13.1 g (60 mmol) of di-tert-butyl dicarbonate and 12.72 g (120 mmol) of sodium carbonate and the mixture is stirred at room temperature for 16 h. The dioxane is then distilled off on a rotary evaporator and the residual aqueous suspension is covered with a layer of 200 ml of ethyl acetate. The mixture is cooled to 5° C., acidified to pH 3 using 1 N HCl and the organic phase is separated off. This is washed twice with saturated NaCl solution and dried over sodium sulfate. After filtering off the drying agent, the filtrate is evaporated under reduced pressure.

Yield: 18.1 g (94% of theory) Purity/isomer distribution: HPLC determination: Nucleosil RP 18, 125×4 mm, 254 nm, acetonitrile/0.1 M phosphoric acid 5:95 to 70:30; 6-isomer: retention time 14.19 min., 7-isomer: retention time 14.72 min. Ratio approximately 1:9; Purity: 99.0%; $^1$H-NMR: (200 MHz) 1.4 (2 s, 9 H); 3.3 (m, 2 H); 4.4–5.0 (3 m, 3 H); 7.4–8.2 (5 m, 3 H); 12.7 (s, 1 H)

EXAMPLE 3

Dicyclohexylammonium 2-tert-butoxycarbonyl-7-nitro-1,2,3,4-tetrahydroisoquinoline-(R)-3-carboxylate To separate the regioisomers, 10 g of the compound from Example 2 are dissolved in 300 ml of ethyl acetate and are treated at room temperature with 1 eq. (6.2 ml) of dicyclohexylamine in 10 ml of ethyl acetate. In the cold, after addition of n-heptane, the dicyclohexylammonium salt slowly crystallizes out, and is filtered off after 16 h and dried. After two further recrystallizations, the proportion of the 6-isomer is less than 1.0% with a total purity of greater than 99%. Further material can be obtained from the mother liquors.

Yield: 6.1 g (1st fraction); Purity/isomer distribution: HPLC determination: Nucleosil RP 18, 125×4 mm, 254 nm, acetonitrile/0.1 M phosphoric acid 5:95 to 70:30; 6-isomer: retention time 13.51 min., 7-isomer: retention time 14.23 min. Ratio>1:99; $^1$H-NMR: (200 MHz) 0.9–1.9 (several m, about 30 H); 2.7–3.05; 3.4; 4.6 (5 m, about 5 H); 7.4; 8.0 (2 m, 3 H); Specific rotation: −23.6° (MeOH, c=1)

EXAMPLE 4

2-tert-Butoxycarbonyl-7-nitro-1,2,3,4-tetrahydroisoquinoline-(R)-3-carboxylic acid To liberate the protected amino acid, the DCHA salt from Example 3 is dissolved in ethyl acetate and extracted by shaking with an excess of aqueous, 10% strength citric acid solution. The organic phase is extracted by shaking with saturated NaCl solution, dried over sodium sulfate and evaporated under reduced pressure.

Yield: between 87 and 95%; $^1$H-NMR: The characteristic signals of dicyclohexylamine are absent. The compound liberated is immediately further processed.

EXAMPLE 5

7-Nitro-1,2,3,4-tetrahydroisoquinoline-(R)-3-carboxylic acid hydrochloride 0.5 g of the compound from Example 4 (1.55 mmol) is treated with 19 ml of HCl in ether and the mixture is stirred at RT for 30 min, evaporated to dryness, coevaporated several times with toluene and dried under reduced pressure.

Yield: 0.385 g (96% of theory); $^1$H-NMR: (200 MHz) 3.2–3.6 (m, 2 H); 4.3–4.6 (m, 3 H); 7.6 (d, 1 H); 8.1 (dd, 1 H); 8.3 (d, 1 h); 10.5 (s, br., 1 H) MS: 223.1 (M+H); Specific rotation: +143.5° (c=1, MeOH)

EXAMPLE 6

2-tert-Butoxycarbonyl-7-amino-1,2,3,4-tetrahydroisoquinoline-(R)-3-carboxylic acid 38 g of the nitro compound from Example 4 (117 mmol) are hydrogenated in a Parr apparatus at RT and a slight excess pressure for 7 h with 2 g of 10% Pd on C in methanol. After evaporating the solvent, the residue is washed with diisopropyl ether and recrystallized from water/ethanol and finally dried under reduced pressure.

Yield: 33 9 (95% of theory); $^1$H-NMR: (200 MHz) 1.4 (2 s, 9 H); 2.9 (m, 2 H); 4.2–4.8 (several m, 3 H); 6.4 (m, 2 H); 6.8 (m, 1 H). MS: 293.1 (M+H); Specific rotation: +28.33° (c=1, methanol)

EXAMPLE 7

2-tert-Butoxycarbonyl-(6/7)-amino-1,2,3,4-tetrahydroisoquinoline-(R)-3-carboxylic acid For reduction of the amino acid from Example 2, the procedure is as described in Example 6. The crude product is evaporated under reduced pressure.

$^1$H-NMR: (200 MHz) 1.4 (2 s, 9 H); 2.9 (m, 2 H); 4.2–4.8 (several m, 3 H); 6.4 (m, broad, 2 H); 6.8 (m, 1 H). MS: 293.1 (M+H)

EXAMPLE 8

2-tert-Butoxycarbonyl-7-amino-1,2,3,4-tetrahydroisoquinoline-(R)-3-carboxylic acid (alternative process)

The isomer mixture from Example 7 is treated with acetonitrile at boiling heat. After cooling, it is filtered off. This treatment is carried out 2–3 times.

$^1$H-NMR: (200 MHz) 1.4 (2 s, 9 H); 2.9 (m, 2 H); 4.2–4.8 (several m, 3 H); 6.4 (m, 2 H); 6.8 (m, 1 H); no difference from Example 6. MS: 293.1 (M+H); Specific rotation: +28.13° (c=1, methanol)

EXAMPLE 9

7-Amino-1,2,3,4-tetrahydroisoquinoline-(R)-3-carboxylic acid dihydrochloride 0.5 g (1.7 mmol) of the compound from Example 8 are treated with HCl in ether for 30 min at RT. After evaporating under reduced pressure, the residue is coevaporated with toluene and the product is freed from solvent residues in an oil-pump vacuum.

Yield: 0.41 g (91% of theory); $^1$H-NMR: (200 MHz) 3.0–3.5 (m, 2 H); 4.2–4.5 (m, 3 H); 7.1–7.4 (2 m, 3H); 10.0 (s, broad, 1 H); MS: 193.0 (M+H); Specific rotation: +86.3° (c=1, methanol)

EXAMPLE 10

2-(4-Methoxybenzenesulfonyl)-7-amino-1,2,3,4-tetrahydroisoquinoline-(R)-3-(N-hydroxy)carboxamide 2-(4-Methoxybenzenesulfonyl)-7-(tert-butoxycarbonyl)-amino-1,2,3,4-tetrahydroiso-quinoline-(R)-3-carboxylic acid is obtained under standard conditions, which are known to the person skilled in the art, from the compound mentioned in Example 1 by the route mentioned in process variant a) (sulfonamide formation using 4-methoxybenzenesulfonyl chloride, chromatographic purification of the 6-/7-isomers (See Example 13 below), reduction of the nitro group to the amino group (See Example 12 below) and introduction of the Boc protective group).

To prepare the hydroxamic acid, 10 g (22 mmol) of 2-(4-methoxybenzenesulfonyl)-7-(tert-butoxycarbonyl)amino-1,2,3,4-tetrahydroisoquinoline-(R)-3-carboxylic acid are dissolved in 100 ml of tetrahydrofuran ("THF"), cooled to −15° C. and treated successively with 2.1 ml (22 mmol) of ethyl chloroformate, 4.8 ml (44 mmol) of N-methylmorpholine and, after 45 min at this temperature, with 13.5 ml (110 mmol) of O-trimethylsilylhydroxylamine. The mixture is additionally stirred for 3 h at RT, the solvent is removed under reduced pressure, the residue is taken up in ethyl acetate and extracted by shaking successively with 10% strength citric acid solution, 10% strength sodium carbonate solution and saturated NaCl solution, dried over sodium sulfate and evaporated in a rotary evaporator, and solvent residues are removed in an oil-pump vacuum.

2.6 g of this compound (total yield 9.1 g), illustrated by the formula identified in Example 11, are treated, after chromatographic purification, with 50 ml of HCl in diethyl ether and the mixture is stirred at RT for 30 min. It is then evaporated under reduced pressure and the residue is coevaporated with toluene.

Yield: 1.97 g (89% of theory); $^1$H-NMR: 2.75 (m, 2 H); 3.8 (s, 3 H); 4.40 (m, 3 H); 6.9–7.3 (m, 3 H); 7.0; 7.7 (2 d, 4 H); 8.8; 9.3; 10.7 (3 s, 3 H)

The compounds mentioned in Table 1 below have been prepared analogously to the preceding Examples.

TABLE 1

| Ex. No. | Structure | Comment | MS (M + H) |
|---|---|---|---|
| 11 | tert-butyl carbamate-substituted tetrahydroisoquinoline-3-carboxylic acid hydroxyamide with 4-methoxyphenylsulfonyl group (Chiral) | R-isomer | 478.1 |
| 12 | 7-amino-tetrahydroisoquinoline-3-carboxylic acid with 4-methoxyphenylsulfonyl group, HCl salt (Chiral) | R-isomer | 331.1 |
| 13 | 7-nitro-tetrahydroisoquinoline-3-carboxylic acid with 4-methoxyphenylsulfonyl group (Chiral) | R-isomer | 393.2 |
| 14 | 7-(alanylamino)-tetrahydroisoquinoline-3-carboxylic acid with 4-methoxyphenylsulfonyl group, HCl salt (Chiral) | R-isomer | 434.2 |

TABLE 1-continued
| Ex. No. | Structure | Comment | MS (M + H) |
|---|---|---|---|
| 15 | 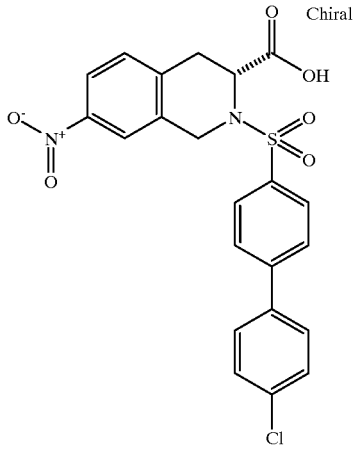 | R-isomer | 473.1 |
| 16 | 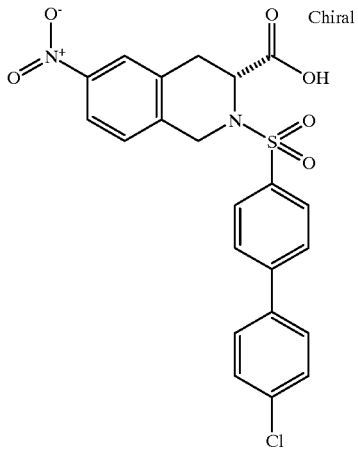 | R-isomer | 473.1 |
| 17 | 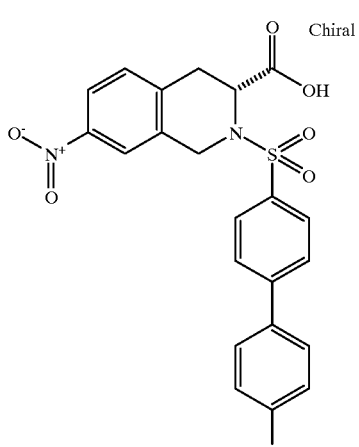 | R-isomer | 457.2 |

TABLE 1-continued
| Ex. No. | Structure | Comment | MS (M + H) |
|---|---|---|---|
| 18 | 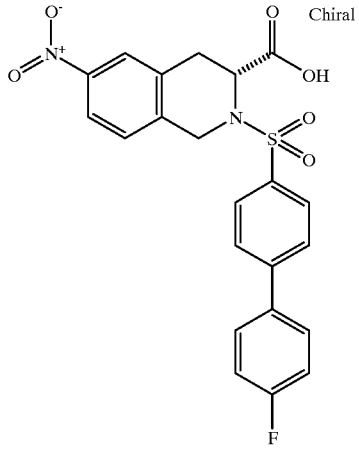 | R-isomer | 457.2 |
| 19 | 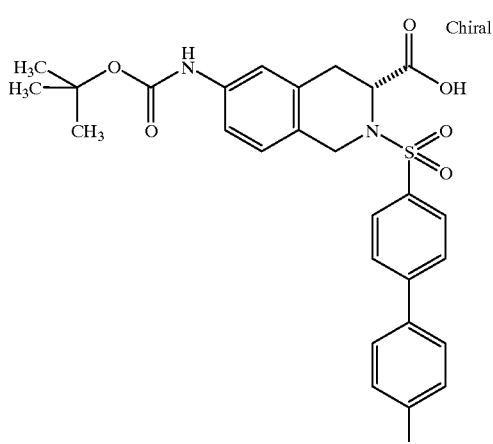 | R-isomer | 542.2 |
| 20 | 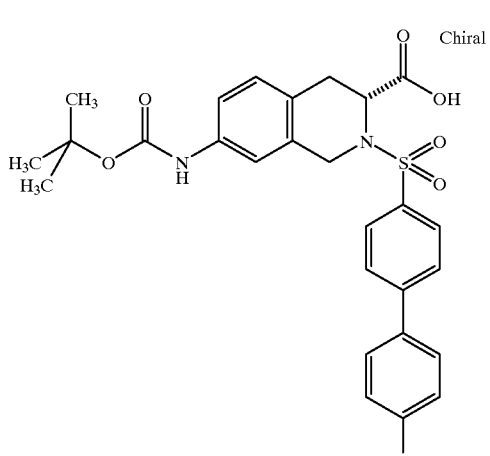 | R-isomer | 527.2 |

TABLE 1-continued

| Ex. No. | Structure | Comment | MS (M + H) |
|---|---|---|---|
| 21 | 6-amino-1,2,3,4-tetrahydroisoquinoline-3-carboxylic acid, 2-[(4'-fluoro-[1,1'-biphenyl]-4-yl)sulfonyl]-, hydrochloride (Chiral) | R-isomer | 427.2 |
| 22 | 7-amino-1,2,3,4-tetrahydroisoquinoline-3-carboxylic acid, 2-[(4'-fluoro-[1,1'-biphenyl]-4-yl)sulfonyl]-, hydrochloride (Chiral) | R-isomer | 427.2 |
| 23 | 7-amino-1,2,3,4-tetrahydroisoquinoline-3-carboxylic acid, 2-[(4'-chloro-[1,1'-biphenyl]-4-yl)sulfonyl]-, hydrochloride (Chiral) | R-isomer | 409.2 |

TABLE 1-continued

| Ex. No. | Structure | Comment | MS (M + H) |
|---|---|---|---|
| 24 | (structure) | R-isomer | 648.2 |
| 25 | (structure) | R-isomer | 514.1 |
| 26 | (structure) | R-isomer | 393.2 |

TABLE 1-continued
| Ex. No. | Structure | Comment | MS (M + H) |
|---|---|---|---|
| 27 | 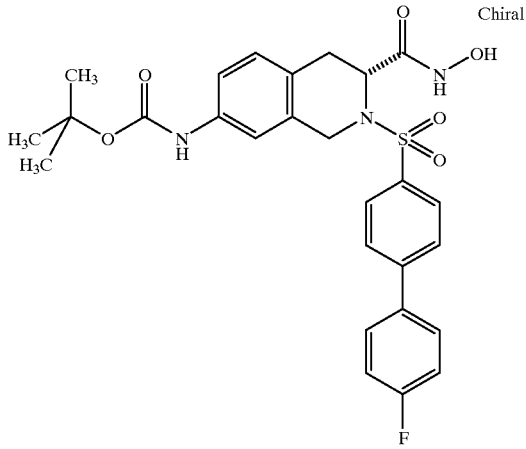 | R-isomer | 542.2 |
| 28 | 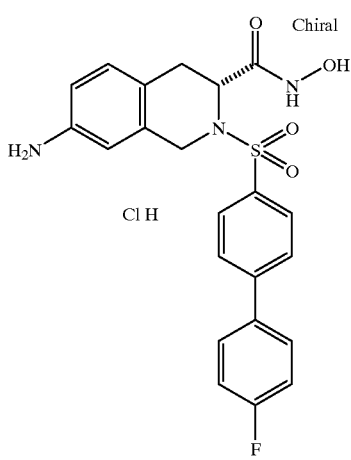 | R-isomer | 442.1 |
| 29 | 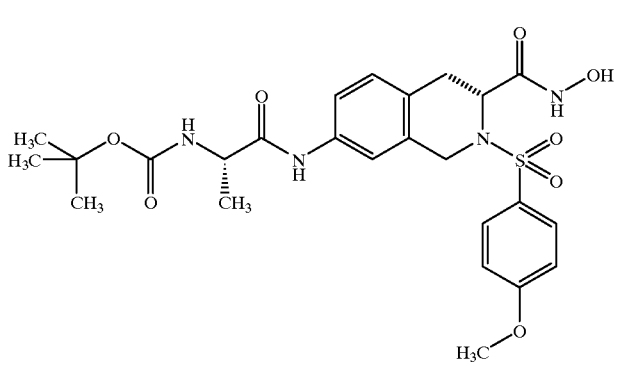 | R-isomer | 449.2 |

TABLE 1-continued

| Ex. No. | Structure | Comment | MS (M + H) |
|---|---|---|---|
| 30 | 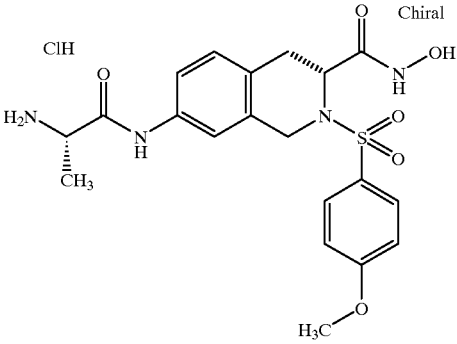 | R-isomer | 449.2 |
| 31 | 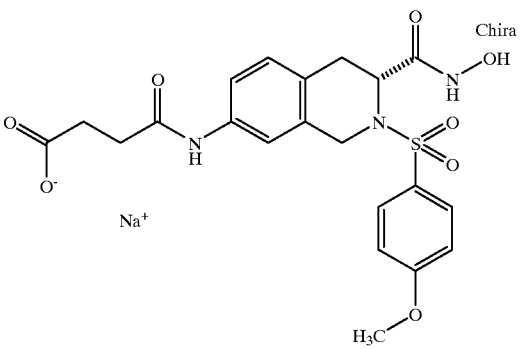 | R-isomer | 478.0 |
| 32 | 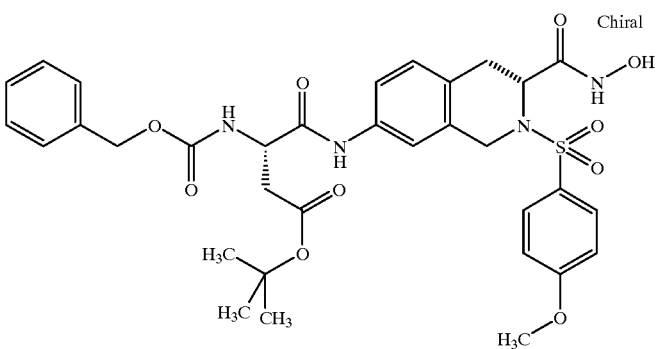 | R-isomer | 683.3 |

Pharmacological Examples

Preparation and determination of the enzymatic activity of the catalytic domains of human stromelysin and of neutrophil collagenase.

The two enzymes—stromelysin (MMP-3) and neutrophil collagenase (MMP-8)—were prepared according to Ye et al., Biochemistry, vol. 31, pp. 11231–11235 (1992). To measure the enzyme activity or the enzyme inhibitor action, 70 µl of buffer solution and 10 µl of enzyme solution are incubated for 15 minutes with 10 µl of a 10% strength (v/v) aqueous dimethyl sulfoxide solution, which optionally contains the enzyme inhibitor. After addition of 10 µl of a 10% strength (v/v) aqueous dimethyl sulfoxide solution which contains 1 mmol/l of the substrate, the enzyme reaction is monitored by fluorescence spectroscopy (328 nm (ex)/393 nm (em)).

The buffer solution contains 0.05% Brij (Sigma, Deisenhofen, Germany) and also 0.1 mol/l tris/HCl, 0.1 mol/l NaCl, 0.01 mol/l $CaCl_2$ and 0.1 mol/l piperazine-N, N'-bis[2-ethanesulfonic acid] (pH=6.5). The enzyme solution contains 5 µg/ml of one of the enzyme domains prepared according to Ye et al. The substrate solution contains 1 mmol/l of the fluorogenic substrate (7-methoxycoumarin4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany).

The enzyme activity is shown as the extinction increase/minute. The $IC_{50}$ values listed in Table 2 are determined as those inhibitor concentrations which in each case lead to a 50% inhibition of the enzyme.

TABLE 2

| Ex. No. | MMP-3 | MMP-8 |
|---|---|---|
| 10 | $1 \times 10^{-8}$ | $2 \times 10^{-9}$ |
| 11 | $2 \times 10^{-8}$ | $3 \times 10^{-9}$ |
| 15 | $6 \times 10^{-7}$ | $3 \times 10^{-8}$ |
| 16 | $5 \times 10^{-7}$ | $2 \times 10^{-8}$ |
| 17 | $1 \times 10^{-6}$ | $4 \times 10^{-8}$ |
| 18 | $5 \times 10^{-7}$ | $2 \times 10^{-8}$ |
| 19 | $4 \times 10^{-7}$ | $3 \times 10^{-8}$ |
| 20 | $2 \times 10^{-6}$ | $1 \times 10^{-7}$ |
| 21 | $2 \times 10^{-7}$ | $8 \times 10^{-9}$ |
| 22 | $3 \times 10^{-7}$ | $8 \times 10^{-9}$ |
| 23 | $2 \times 10^{-7}$ | $7 \times 10^{-9}$ |
| 24 | $3 \times 10^{-7}$ | $6 \times 10^{-8}$ |
| 25 | $2 \times 10^{-7}$ | $1 \times 10^{-8}$ |
| 26 | $8 \times 10^{-8}$ | $8 \times 10^{-9}$ |
| 27 | $1 \times 10^{-7}$ | $1 \times 10^{-8}$ |
| 28 | $2 \times 10^{-8}$ | $2 \times 10^{-9}$ |
| 29 | $2 \times 10^{-8}$ | $2 \times 10^{-9}$ |
| 30 | $3 \times 10^{-8}$ | $5 \times 10^{-9}$ |
| 31 | $2 \times 10^{-8}$ | $4 \times 10^{-9}$ |
| 32 | $4 \times 10^{-7}$ | $1 \times 10^{-8}$ |

What is claimed is:

1. A compound of the formula I

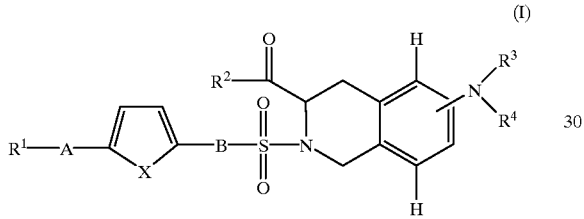

or a stereoisomeric form of the compound of the formula I, or a physiologically tolerable salt of any of the foregoing, where $R^1$ is 1. phenyl;
  2. phenyl which is mono- or disubstituted by
    2.1. ($C_1$–$C_6$)-alkyl, which is linear, cyclic or branched,
    2.2. —OH,
    2.3. ($C_1$–$C_6$)-alkyl-C(O)—O—,
    2.4. ($C_1$–$C_6$)-alkyl-O—,
    2.5. ($C_1$–$C_6$)-alkyl-O—($C_1$–$C_4$)-alkyl-O—,
    2.6. halogen,
    2.7. —$CF_3$,
    2.8. —CN,
    2.9. —$NO_2$,
    2.10. HO—C(O)—,
    2.11. ($C_1$–$C_6$)-alkyl-O—C(O)—,
    2.12. methylenedioxo,
    2.13. $R^5$—($R^6$)N—C(O)—, in which $R^5$ and $R^6$ are identical or different and represent a hydrogen atom or ($C_1$–$C_6$)-alkyl-, or
    2.14. $R^5$—($R^6$)N—, in which $R^5$ and $R^6$ are identical or different and represent a hydrogen atom or ($C_1$–$C_6$)-alkyl-;
  3. a heteroaromatic from the following group 3.1. to 3.15., which is unsubstituted or substituted as described under 2.1 to 2.14,
    3.1. pyrrole,
    3.2. pyrazole,
    3.3. imidazole,
    3.4. triazole,
    3.5. thiophene,
    3.6. thiazole,
    3.7. oxazole,
    3.8. isoxazole,
    3.9. pyridine,
    3.10. pyrimidine,
    3.11. indole,
    3.12 benzothiophene,
    3.13. benzimidazole,
    3.14. benzoxazole, or
    3.15. benzothiazole;
  4. —OH and A is a covalent bond;
  5. —O—$R^{14}$ and A is a covalent bond, —CH=CH— or —C≡C—
    and in which $R^{14}$ is
    1) ($C_1$–$C_6$)-alkyl,
    2) ($C_3$–$C_6$)-cycloalkyl,
    3) benzyl, or
    4) phenyl;
  6. —COOH and A is a covalent bond, —CH=CH— or —C≡C—;
  7. ($C_1$–$C_6$)-alkyl;
  8. ($C_3$–$C_6$)-cycloalkyl-O—($C_1$–$C_4$)-alkyl;
  9. halogen and A is a covalent bond, —CH=CH— or —C≡C—;
  10. —CN and A is a covalent bond, —CH=CH— or —C≡C—;
  11. —$NO_2$ and A is a covalent bond, —CH=CH— or —C≡C—; or
  12. —$CF_3$; and $R^2$ is 1. HO(H)N—; or
  2. $R^7$—O—, in which $R^7$ is
    2.1 a hydrogen atom,
    2.2 ($C_1$–$C_6$)-alkyl,
    2.3 allyl, or
    2.4 benzyl;

$R^3$ and $R^4$ are identical or different and are
  1. hydrogen,
  2. ($C_1$–$C_6$)-alkyl,
  3. phenyl-$(CH_2)_m$—, in which phenyl is unsubstituted or mono- or disubstituted as described under 2.1 to 2.14. and m is the integer zero, 1, 2, or 3,
  4. $R^8$—(CO)—, in which $R^8$ is
    4.1 ($C_1$–$C_8$)-alkyl,
    4.2 phenyl-$(CH_2)_m$—, in which phenyl is unsubstituted or mono- or disubstituted as described under 2.1. to 2.14. and m is the integer zero, 1, 2, or 3,
    4.3 $R^7$—O—C(O)—$(CH_2)_n$—, in which $R^7$ is as defined above and n is the integer zero, 1, 2, 3, 4, 5, or 6,
    4.4 $R^7$—N(H)—($R^9$)—C(H)—, in which $R^7$ is as defined above and $R^9$ is the characteristic radical of a proteinogenic α-amino acid and in which $R^9$ is unsubstituted or mono- or disubstituted on an oxygen or sulfur atom by ($C_1$–$C_4$)-alkyl, benzyl or allyl or is substituted by an N-protective group,
    4.5 $R^7$—C(O)—N(H)—($R^9$)—C(H)—, in which $R^7$ and $R^9$ are as defined under 4.4, or
    4.6 $R^{10}$—O—C(O)—N(H)—($R^9$)—C(H)—, in which $R^9$ is as defined under 4.4 and $R^{10}$ is
      4.6.1 ($C_1$–$C_6$)-alkyl,
      4.6.2 allyl,
      4.6.3 benzyl, or
      4.6.4 (9-fluorenyl)methyl;
  5. $R^{10}$—O—C(O)—, in which $R^{10}$ is as defined under 4.6.1 to 4.6.4;

6. $R^{15}$—$SO_2$—, in which $R^{15}$ is
   6.1 $(C_1-C_6)$-alkyl,
   6.2 allyl, or
   6.3 phenyl-$(CH_2)_m$—, in which phenyl is unsubstituted or mono- or disubstituted as described under 2.1 to 2.14 and m is the integer zero, 1, 2, or 3; or
7. $H_2N$—$C(=NH)$—; or $R^3$ and $R^4$ together with the nitrogen atom to which they are attached form a radical of the formula $X_a$ or $X_b$,

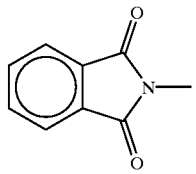

(X$_a$)

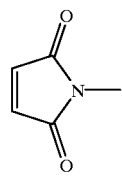

(X$_b$)

or $R^3$ and $R^4$ together with the nitrogen atom to which they are attached form a nitro radical, A is a) a covalent bond,
   b) —O—,
   c) —CH═CH—, or
   d) —C≡C—;

B is a) —$(CH_2)_m$—, in which m has the abovementioned meaning,
   b) —O—$(CH_2)_q$—, in which q is the integer 1, 2, 3, 4, or 5, or
   c) —CH═CH—; and X is —CH═CH—, oxygen, or sulfur.

2. A process for the preparation of a compound of the formula I as claimed in claim 1, which comprises the steps of:

a) converting the compound of the formula II

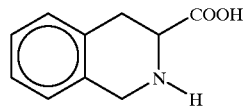

(II)

into a compound of the formula III,

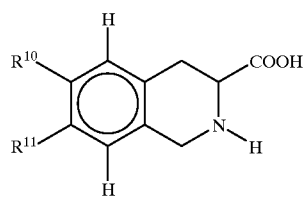

(III)

in which $R^{10}$ and $R^{11}$ are —$NO_2$ or a hydrogen atom and $R^{10}$ and $R^{11}$ are not identical, and b) reacting the compound of the formula III obtained in a) with the compound of the formula IV

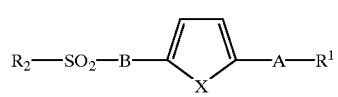

(IV)

in which B, X, A, and $R^1$ are as defined in formula I of claim 1 and $R_2$ is a chlorine atom, imidazolyl, or —OH, in the presence of a base or, if appropriate, a dehydrating agent to give a compound of the formula V

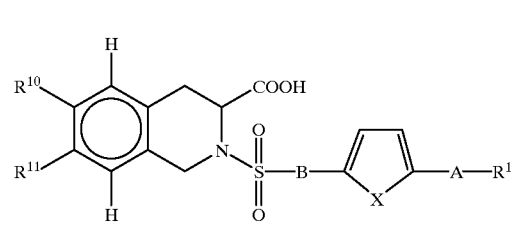

(V)

in which $R^{10}$ and $R^{11}$ are —$NO_2$ or a hydrogen atom and $R^{10}$ and $R^{11}$ are not identical, and c) subjecting the compound of the formula V obtained in b) to an isomer separation and obtaining a compound of the formula I in which $R^3$ and $R^4$ together with the nitrogen atom to which they are attached form an $NO_2$ radical which binds to the phenyl radical in position 6 or 7, or d) reducing the compound obtained in c) to a compound of the formula I in which $R^3$ and $R^4$ are hydrogen, or e) acylating a compound obtained in d) with a carbonyl or sulfonyl chloride, carboxylic or sulfonic imidazolide, chloroformic acid ester, active ester or anhydride, or f) reacting a compound obtained in d) with the appropriate amino acid, carboxylic acid, aldehyde, or optionally substituted guanidine, or g) alkylating a compound obtained in d), or h) reacting a compound obtained in a) to give a compound of the formula VI,

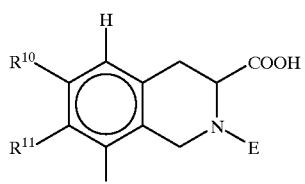

(VI)

in which E is a N-protective group and $R^{10}$ and $R^{11}$ are as defined above, and separating the compound of the formula VI into the regioisomers of the formulae VI and VIII

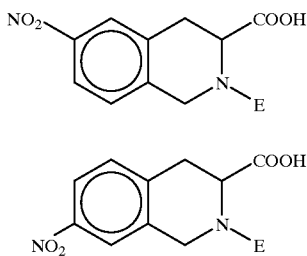

and reacting the nitro group as described under d) and reacting the compound obtained as under e), f) or g), or i) reacting a compound obtained by the process d), e), f), g) or h) to give the corresponding carboxylic acid ester ($R^2$=O—$R^7$), in which $R^7$ is as defined in formula I of claim 1, or j) reacting a compound obtained by the process d), e), f), g) or h) with hydroxylamine ($R^2$=—N(H)—OH).

3. A pharmaceutical composition comprising an effective amount of at least one compound of the formula I as claimed in claim 1, a stereoisomeric form of said compound, or a physiologically tolerable salt of said compound or its steroisomeric form, together with a pharmaceutically suitable and physiologically tolerable carrier, additive, or other compound or auxiliary.

4. A method for the prophylaxis or therapy of a disorder involving increased activity of matrix-degrading metalloproteinases, which comprises administering to a host in need of such prophylaxis or therapy a pharmaceutical composition as claimed in claim 3.

5. A method for the prophylaxis or therapy of a disorder involving increased activity of matrix-degrading metalloproteinases, which comprises administering to a host in need of such prophylaxis or therapy an effective amount of at least one compound of the formula I as claimed in claim 1, a stereoisomeric form of said compound, or a physiologically tolerable salt of said compound or its stereoisomeric form.

6. A method as claimed in claim 5, wherein the disorder is a degenerative joint disorder.

7. A method as claimed in claim 6, wherein the disorder is osteoarthrosis, spondylosis, or chondrolysis after joint trauma or relatively long joint immobilization after meniscus or patella injury or ligament tear.

8. A method as claimed in claim 5, wherein the disorder is a disorder of the connective tissue.

9. A method as claimed in claim 8, wherein the disorder is collagenosis, a periodontal disorder, a wound healing disorder, or a chronic disorder of the locomotory apparatus.

10. A method as claimed in claim 9, wherein the disorder is an inflammatory, immunologically or metabolically related acute or chronic arthritis, arthropathy, myalgia, or disorder of the bone metabolism.

11. A method as claimed in claim 5, wherein the disorder is an ulceration, atherosclerosis, or stenosis.

12. A method as claimed in claim 5, wherein the disorder is inflammation, carcinomatosis, formation of tumor metastases, cachexia, anorexia, or septic shock.

13. A process for the production of a pharmaceutical as claimed in claim 3, which comprises bringing at least one compound of the formula I as claimed in claim 1 into a suitable administration form with a physiologically acceptable auxiliary and carrier, with or without a further additive or other compound.

* * * * *